United States Patent
Navia et al.

(10) Patent No.: US 6,626,872 B1
(45) Date of Patent: Sep. 30, 2003

(54) PERFUSION CANNULA

(76) Inventors: Jose A. Navia, Suipacha 1308-4B, 1011 Buenos Aires (AR); Jorge L. Jordana, Juana Azurduy 2304, 1429 Buenos Aires (AR)

(*) Notice: Subject to any disclaimer, the term of this patent is extended or adjusted under 35 U.S.C. 154(b) by 0 days.

(21) Appl. No.: 09/659,937

(22) Filed: Sep. 12, 2000

(51) Int. Cl.⁷ .............................................. A61M 25/00
(52) U.S. Cl. ..................................................... 604/264
(58) Field of Search ................................ 604/264, 523, 604/532, 289, 525

(56) References Cited

U.S. PATENT DOCUMENTS

| | | | |
|---|---|---|---|
| 4,142,528 A | 3/1979 | Whelan, Jr. et al. | .... 128/350 R |
| 4,168,708 A | 9/1979 | Lepley, Jr. et al. | ......... 128/325 |
| 4,230,119 A | 10/1980 | Blum | ......................... 128/325 |
| 4,946,463 A | 8/1990 | Wright | ....................... 606/158 |
| 5,184,610 A | 2/1993 | Marten et al. | ......... 128/207.14 |
| 5,334,169 A * | 8/1994 | Brown et al. | ............... 604/265 |
| 5,462,523 A * | 10/1995 | Samson et al. | ............. 604/246 |
| 5,759,173 A * | 6/1998 | Preissman et al. | ..... 604/103.07 |
| 5,807,356 A * | 9/1998 | Finch et al. | ................. 604/247 |
| 5,928,192 A | 7/1999 | Maahs | .......................... 604/96 |
| 5,947,919 A | 9/1999 | Krueger et al. | ................. 604/8 |
| 6,053,901 A | 4/2000 | Finch et al. | ................. 604/502 |
| 6,066,100 A * | 5/2000 | Willard et al. | ............... 600/452 |
| 6,095,997 A * | 8/2000 | French et al. | ................ 604/104 |
| 6,136,025 A * | 10/2000 | Barbut et al. | ............... 604/530 |
| 6,331,176 B1 * | 12/2001 | Becker et al. | ............... 604/533 |

FOREIGN PATENT DOCUMENTS

| | | |
|---|---|---|
| EP | 0791332 A1 | 2/1997 |
| EP | 1025876 A2 | 1/2000 |

* cited by examiner

*Primary Examiner*—William E. Tapolcai
*Assistant Examiner*—Mohammad M. Ali
(74) *Attorney, Agent, or Firm*—Coudert Brothers LLP

(57) ABSTRACT

A perfusion cannula having a proximal section configured for attachment to a source of perfusion fluid, and a distal section configured for insertion in a blood vessel for delivering perfusion fluid to the blood vessel. In one embodiment, the cannula generally comprises a shaft having a proximal end, a distal end, a distal shaft section, and a proximal shaft section which is connected to the distal shaft section between the proximal and distal ends of the distal shaft section such that an acute angle is formed between the proximal shaft section and the proximal end of the distal shaft section. A lumen in the elongated shaft extends within the proximal shaft section and the distal shaft section to and in fluid communication with a port in the distal end of the distal shaft section. The lumen is configured for delivery of fluid, and may be configured for slidably receiving a guidewire therein.

26 Claims, 6 Drawing Sheets

PERFUSION CANNULA

BACKGROUND OF THE INVENTION

This invention relates to the field of intraluminal devices, and more particularly to cannulas for delivery of fluid to a patient's body lumen.

Vascular anastomoses, in which two vessels are surgically joined together to form a continuous channel, are required for a variety of conditions including coronary artery disease, diseases of the great and peripheral vessels, organ transplantation, and trauma. For example, in coronary artery disease, an occlusion or stenosis in a coronary artery interferes with blood flow to the heart muscle. In order to restore adequate blood flow to the heart, a graft vessel in the form of a prosthesis or harvested artery or vein is used to reroute blood flow around the occlusion. The treatment, known as coronary artery bypass grafting (CABG), can be highly traumatic to the patient's system.

In conventional CABG a large incision is made in the chest and the sternum is sawed in half to allow access to the heart. In addition, cardiopulmonary bypass, in which the patient's blood is circulated outside of the body through a heart-lung machine, is used so that the heart can be stopped and the anastomosis performed. In order to minimize the trauma to the patient's system induced by conventional CABG, less invasive techniques have been developed in which the surgery is performed through small incisions in the patient's chest with the aid of visualizing scopes. Less invasive CABG can be performed on a beating or a non-beating heart, and may avoid the need for cardiopulmonary bypass.

During beating heart surgery, the oxygen requirement of the cardiac muscle is high and any interruption in the coronary flow of blood may result in iscehmia, heamodynamic unstability, ventricular arrythmias, stunned myocardium, or myocardial infarction. However, during coronary bypass surgery, it is necessary to interrupt the flow of blood to the myocardium which is distal (i.e., downstream) to the anastomosis site while the bypass graft is sutured to the coronary artery. As a result, the myocardium distal to the anastomosis site is deprived of oxygen until the suturing is completed and the flow across the bypass graft is established. Intracoronary shunts placed at the anastomosis site have been used to allow the native coronary flow to continue irrigating the distal myocardium during the bypass surgery. The shunt may have enlarged tips to occlude the coronary vessel on either side of the anastomosis site, to keep the site clean of blood during suturing. However, the supply of blood to the distal myocardium is poor due to the presence of the lesion in the coronary artery. An alternative method of perfusing distal to the anastomosis site is the use of an intracoronary perfusion cannula, introduced into the coronary artery at the anastomosis site to deliver oxygenated blood from the patient's aorta or other source. However, one difficulty has been insertion of the cannula into the coronary artery, and the tendency of such cannula to back out of the coronary artery during perfusion due to the back pressure from the blood.

What has been needed is a perfusion cannula providing improved perfusion of a patient's blood vessel distal to an anastomosis site.

SUMMARY OF THE INVENTION

The invention is directed to a perfusion cannula having a proximal section configured for attachment to a source of perfusion fluid, and a distal section configured for insertion in a blood vessel, for delivering perfusion fluid to the blood vessel. The term distal as used herein should be understood to mean downstream in relation to flow of fluid within a vessel, or farther away from the physician in relation to a device manipulated by the physician. The term proximal as used herein should be understood to mean upstream in relation to flow of fluid within a vessel, or closer to the physician in relation to a device manipulated by the physician.

In one embodiment, the cannula generally comprises a shaft having a proximal end, a distal end, a distal shaft section, and a proximal shaft section which is connected to the distal shaft section between the proximal and distal ends of the distal shaft section such that an acute angle is formed between the proximal shaft section and a proximal portion of the distal shaft section. The acute angle is measured at the location at which the proximal shaft section is connected to the distal shaft section. A lumen in the elongated shaft extends within the proximal shaft section and within at least a portion of the distal shaft section, to and in fluid communication with a port in the distal end of the distal shaft section. The lumen is configured for delivery of fluid, and may be configured for slidably receiving a guidewire therein. Thus, with the proximal end of the cannula attached to a source of perfusion fluid, such as the patient's aorta, and the distal shaft section inserted within a native blood vessel, such as a coronary artery, through a surgical incision in a wall of the blood vessel, the acute angle causes the cannula to hook or wedge onto the wall of the blood vessel at the proximal end of the incision, so that the distal shaft section is securely anchored within the blood vessel during the perfusion. Unlike a perpendicular or nearly perpendicular angle, the acute angle of the invention sandwiches the wall of the native blood vessel between the shaft sections, with a distal length of the proximal shaft section adjacent to, or preferably in contact with, an outer surface of the native blood vessel.

In one embodiment, the cannula has at least one of a proximal occluder on a proximal portion of the distal shaft section and a distal occluder on a distal portion of the distal shaft section. The distal occluder avoids leaks of the pressurized perfusion fluid around the outer surface of the distal shaft section and into the site proximal to the distal occluder. The proximal occluder occludes the blood flow from a proximal section of the native blood vessel, and provides anchoring for the cannula to prevent or inhibit the cannula from being pushed back proximally from the blood vessel by the pressure of the perfusion flow.

In one embodiment, the distal shaft section of the cannula has a lumen only within a distal portion of the distal shaft section, so that the cannula delivers perfusion fluid to the native blood vessel out the port in the distal end of the cannula. Thus, the proximal portion of the distal shaft section is a solid walled blind tube or plug, which does not allow for flow of fluid therein. The terminology blind tube as used herein should be understood to mean a member which does not have a lumen in fluid communication with ports therein which provides a fluid delivery channel through the member. Thus, in the embodiment having one or more occluders on the distal shaft section, the cannula prevents the flow of blood within the native blood vessel at the site of the distal shaft section and retrograde flow of perfusion fluid. As a result, retrograde flow of the perfusion fluid out the proximal end of the distal shaft section, that could dislodge plaque and produce embolization of particles, is avoided. In an alternative embodiment, the distal shaft section has a lumen in the proximal portion of the distal shaft section in fluid communication with the lumen in the distal portion of the distal shaft section, so that the distal shaft section provides a shunt which channels the blood flow of the native blood vessel through the lumen in the distal shaft section, or retrograde flow of perfusion fluid out the proximal portion of the distal shaft section.

One embodiment of the invention is a perfusion cannula generally comprising a shaft having a proximal end, a distal end, a proximal shaft section having a lumen, and a distal shaft section having a proximal portion with a solid proximal end, and a distal portion with a lumen in fluid communication with the proximal shaft section lumen and with a port in the distal end of the distal shaft section. In an embodiment having one or more occluders on the distal shaft section, the cannula prevents the flow of blood within the native blood vessel at the site of the distal shaft section and retrograde flow of perfusion fluid.

In a method of performing a medical procedure, the perfusion cannula of the invention is used to deliver perfusion fluid to a native blood vessel. In a presently preferred method, the distal shaft section of the perfusion cannula is inserted distal to a lesion in the blood vessel for perfusion of the blood vessel distal to an anastomosis site during bypass surgery.

The cannula of the invention, provides easy introduction of the cannula within the patient's blood vessel. Additionally, the cannula provides for secure anchoring of the cannula within a blood vessel during perfusion, due at least in part to the acute angle between the proximal shaft section and the proximal portion of the distal shaft section. Moreover, in the embodiment having a distal shaft section with a solid proximal portion, the cannula of the invention avoids dislodging plaque in the native blood vessel from retrograde flow within or around the cannula distal shaft section. These and other advantages of the invention will become apparent from the following detailed description of the invention and accompanying exemplary figures.

DETAILED DESCRIPTION OF THE INVENTION

Figure 1:
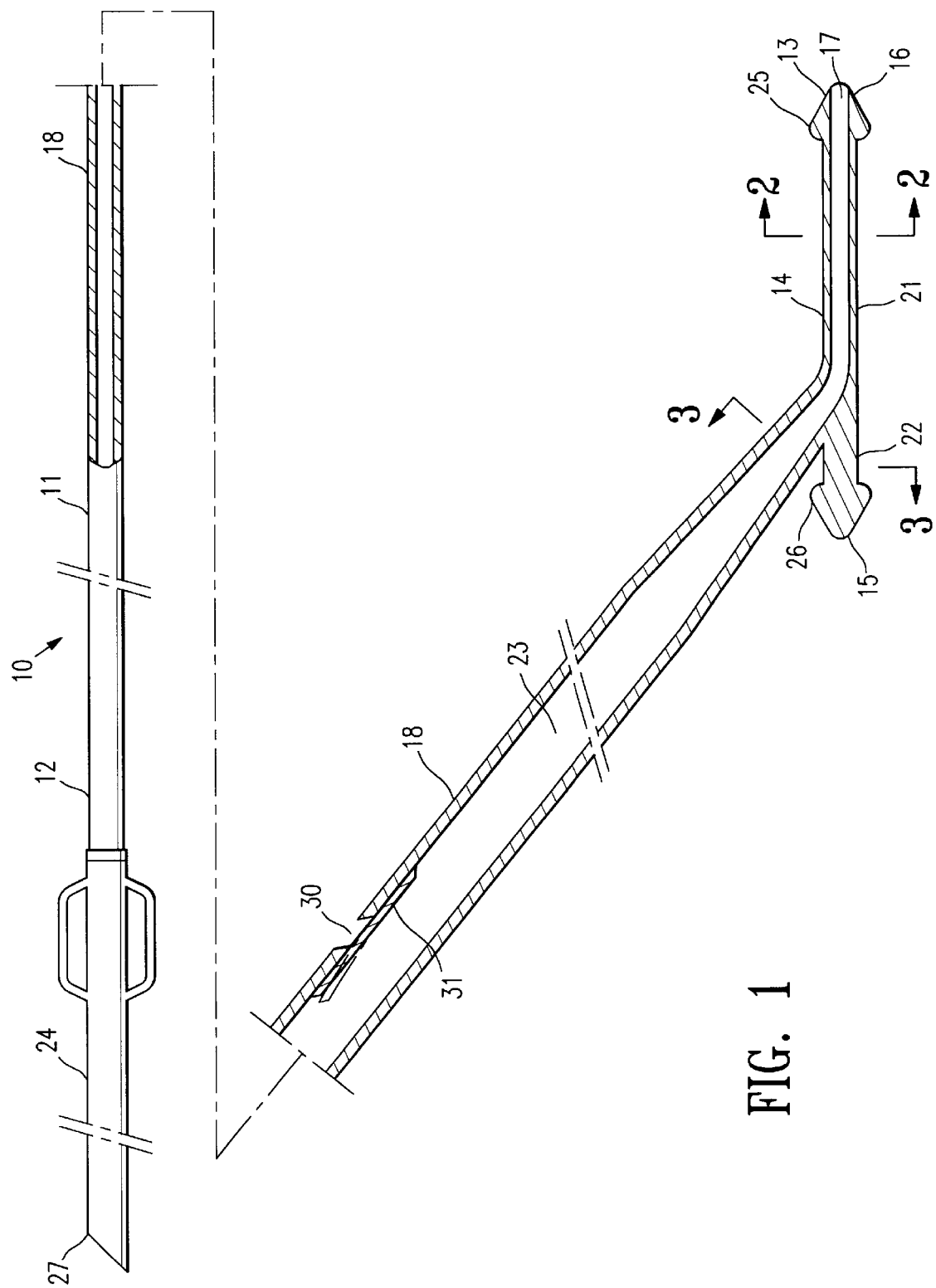
FIG. 1 is an elevational view, partially in section, of perfusion cannula which embodies features of the invention.
Figure 2:
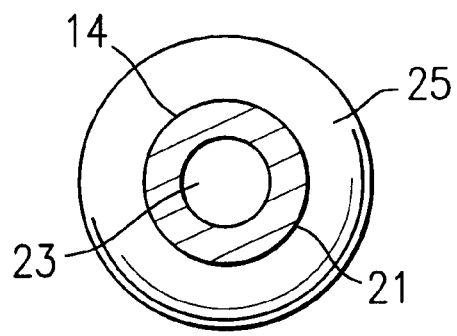
FIG. 2 is a transverse cross-sectional view of the catheter shown in FIG. 1 taken along line 2—2.
Figure 3:
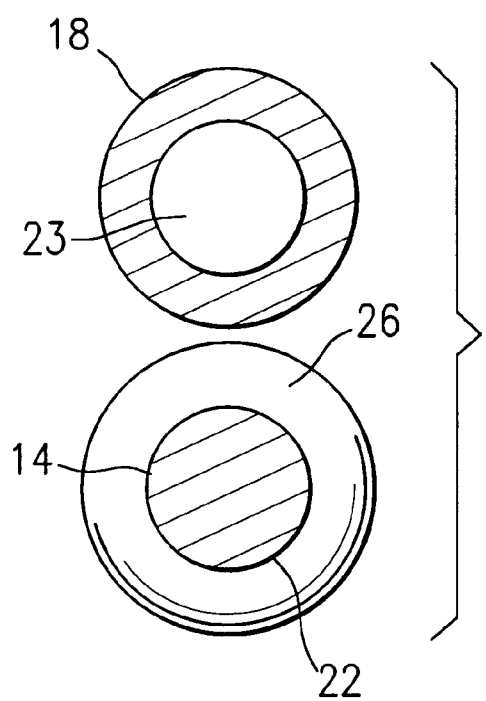
FIG. 3 is a transverse cross-sectional view of the catheter shown in FIG. 1 taken along line 3—3.

In the embodiment illustrated in FIGS. 1–3, the intraluminal cannula 10 of the invention comprises an elongated shaft 11, having a proximal end 12, a distal end 13, a distal shaft section 14 having a proximal end 15, a distal end 16, and a port 17 in the distal end of the distal shaft section 14. A proximal shaft section 18 is connected to the distal shaft section 14 between the proximal end 15 and the distal end 16 of the distal shaft section, such that an acute angle is formed between the proximal shaft section 18 and the proximal end 15 of the distal shaft section at the location at which the proximal shaft section 18 is connected to the distal shaft section 14. The terminology connected to as used herein in relation to the proximal shaft section being connected to the distal shaft section should be understood to include proximal and distal shaft sections which are an integral, one piece unit, or alternatively, a proximal shaft section which is a separate member bonded to the distal shaft section as for example with adhesive or heat bonding. In a presently preferred embodiment, the proximal and distal shaft sections 18 and 14 are an integral, one piece unit. The distal shaft section 14 has a distal portion 21 extending distally from the location at which the proximal shaft section 18 is connected to the distal shaft section 14, and a proximal portion 22 extending proximally from the location at which the proximal shaft section 18 is connected to the distal shaft section 14. A lumen 23 in the elongated shaft 11 extends within the proximal shaft section 18 and the distal shaft section 14 to an in fluid communication with the port 17 in the distal end of the distal shaft section 14. An adapter 24 on the proximal end 12 of the shaft provides access to the lumen 23 and is configured for connection to a source of perfusion fluid. In the embodiment illustrated in FIG. 1, the adapter 24 comprises a needle 27 configured for insertion into a patients blood vessel.

In the embodiment illustrated in FIG. 1, the distal shaft section 14 has a distal occluder 25 on the distal portion 21, and a proximal occluder 26 on the proximal portion 22. In the embodiment illustrated in FIG. 1, each occluder 25/26 comprises a protuberance having a larger outer diameter than a portion of the distal shaft section proximal or distal, respectively, thereto. However, other suitable occluders can be used including self expanding members, or inflatable members such as balloons. In the embodiment illustrated in FIG. 1, occluders 25/26 have a tapered outer diameter, however, a variety of suitable shapes conventionally used for occluders can be used. The lumen 23 in the distal shaft section 14 extends within the distal occluder 25. The proximal occluder 26 is a solid member.

The lumen 23 within the distal shaft section 14 extends within the distal portion 21 of the distal shaft section. In the embodiment illustrated in FIG. 1, the proximal portion 22 of the distal shaft section is a solid walled member with a solid proximal end, which does not have a lumen therein or a port in an outer surface thereof, so that the proximal portion 22 is a blind tube configured to block the flow of perfusion fluid or blood proximally within the distal shaft section. In one embodiment, the proximal portion 22 may have members therein such as blind or dead-end channels or reinforcements.

In the embodiment illustrated in FIG. 1, the proximal shaft section 18 has an intermediate guidewire port 30 between the proximal and distal ends of the shaft. The guidewire port 30 has a blocking member or valve 31, which in the embodiment of FIG. 1 is a flap configured to block flow of perfusion fluid from the shaft lumen 23 through the guidewire port 30. The guidewire port 30 allows a guidewire 32 (FIG. 4) to be laterally inserted into the lumen 23 through a side wall of the proximal shaft section 18.

Figure 4:
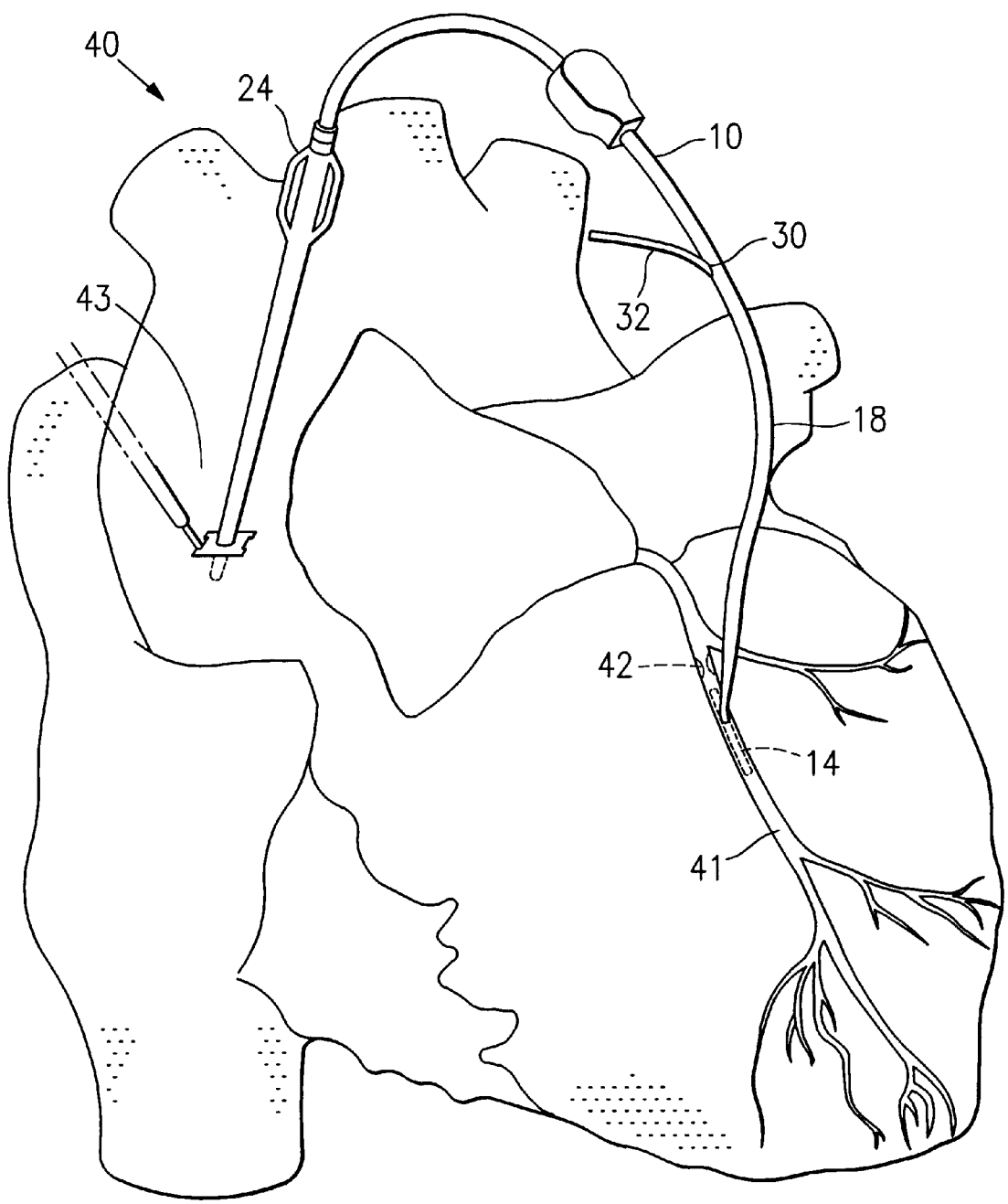
FIG. 4 is an elevation view of a patient's heart, and a perfusion cannula which embodies features of the invention in place on the patient's heart during perfusion of a coronary artery.

The cannula 10 can be used in a method of performing a medical procedure, such as perfusion of a blood vessel during an anastomosis procedure. FIG. 4 illustrates a patient's heart 40 with perfusion cannula 10 in place during perfusion of a coronary artery. The distal shaft section 14 is within a coronary artery 41 distal to a lesion 42 therein, and the proximal end of the needle adapter 24 is within the ascending aorta 43. In a method of using the cannula 10 of the invention, after flushing the cannula, guidewire 32 or other support member such as a mandrel, can be introduced into the lumen 23 of the shaft to give support to the soft distal end of the cannula, to facilitate introducing the distal shaft section into the coronary artery using for example, a Seldinger technique. In the embodiment illustrated in FIG. 4, the guidewire 32 extends from the intermediate guidewire port 30 into the lumen 23, which is closed internally by blocking member 31 to prevent the flow of blood out the guidewire port 30. The distal shaft section 14, preferably with the guidewire 32 therein, is inserted into the coronary artery 41, and perfusion flow initiated either before or after proximally withdrawing the guidewire 32 from the lumen 23 out the guidewire port 30. Alternatively, the proximal end of guidewire 32 may extend out a port in the proximal end of the shaft, and the guidewire 32 removed from the lumen 23 before the proximal end of the shaft is connected to a source of perfusion fluid and perfusion is started. An adapter (not shown) having a guidewire port may be provided on the proximal end of the shaft 11 for providing guidewire access to lumen 23.

Figure 5:
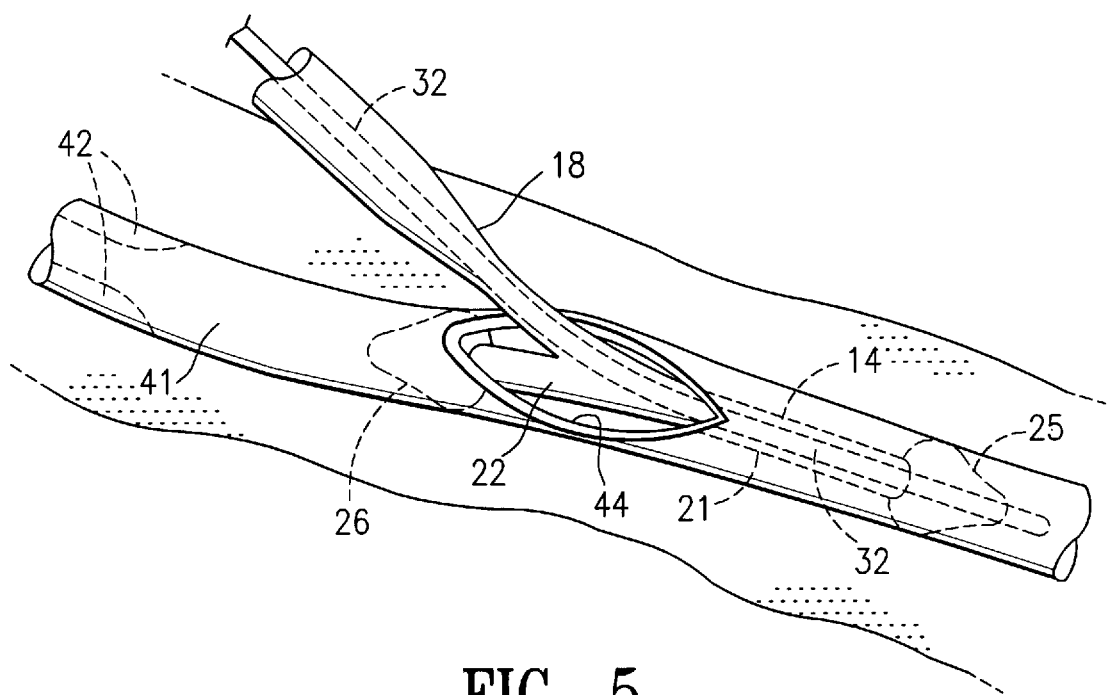
FIG. 5 is an enlarged view, partially in phantom, of the distal end of the perfusion cannula shown in FIG. 1, after insertion within a blood vessel, with a guidewire illustrated in phantom within the cannula lumen.
Figure 6:
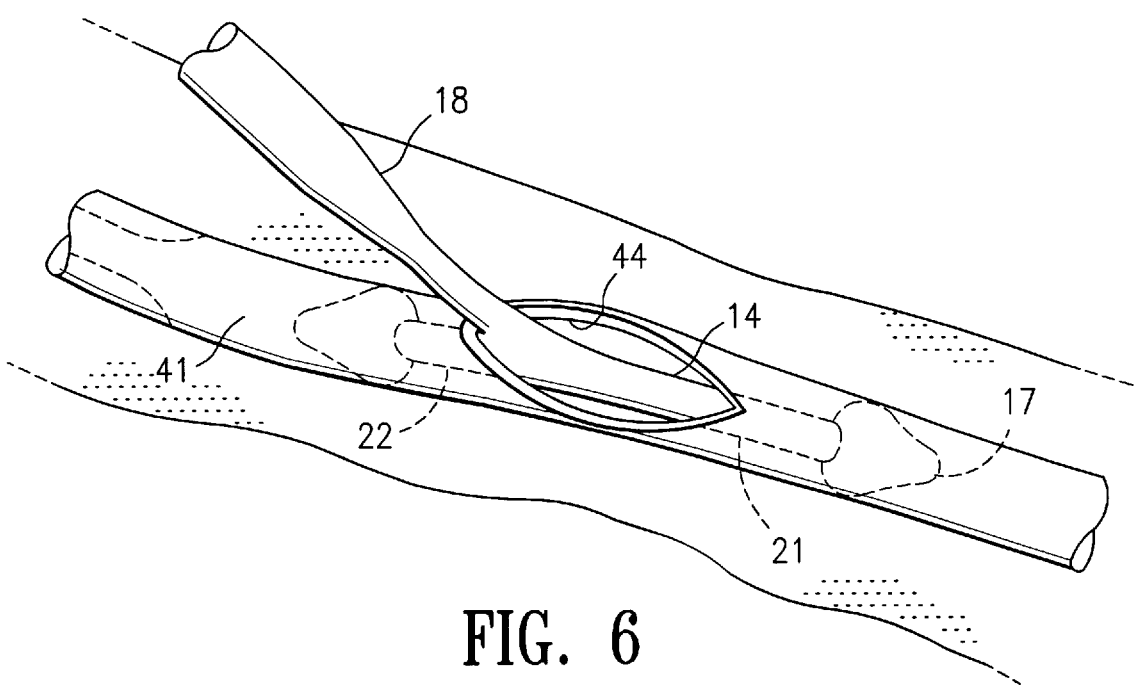
FIG. 6 illustrates the cannula shown in FIG. 5, after the cannula is positioned proximally within the blood vessel and the guidewire removed.

FIGS. 5–8 illustrate the performance of an anastomosis at the site of the distal shaft section 14 of the cannula 10. As illustrated in FIG. 5, the distal shaft section 14 has been inserted through a surgical incision 44 (arteriotomy) or other opening in the coronary artery 41. The cannula 10 is inserted either without a guidewire, or with guidewire 32 (shown in phantom in lumen 23) in the shaft lumen 23 or slidably over a guidewire 32 which has a distal end already in the coronary artery 41. The cannula is displaced proximally within the artery 41 until the portions of the proximal shaft section 18 and proximal portion 22 of the distal shaft section 14 which define the acute angle at the location of the connection between the proximal and distal shaft sections, are adjacent to or in contact with the wall of the artery 41 at the proximal end of the incision 44, as illustrated in FIG. 6. The wall of the artery at the proximal end of the incision 44 is sandwiched between a distal end of the proximal shaft section 18 and the proximal portion 22 of the distal shaft section 14, to anchor the distal shaft section within the coronary artery 41. The anchored distal shaft section 14 prevents or inhibits the proximally thrusting force of the perfusion fluid flowing distally out the port 17 from causing further displacement of the distal shaft section proximally within the artery 41 and out of the incision 44 during perfusion. With the distal shaft section 14 in place within the artery 41, perfusion is started by connecting the proximal end of the cannula to an arterial line, as by inserting the needle adapter 24 into the aorta 43 and allowing blood flow from the aorta, into the adapter 24 and lumen 23 in fluid communication therewith, and out the port 17 in the distal end of the distal shaft section 14 within the coronary artery 41.

Figure 7:
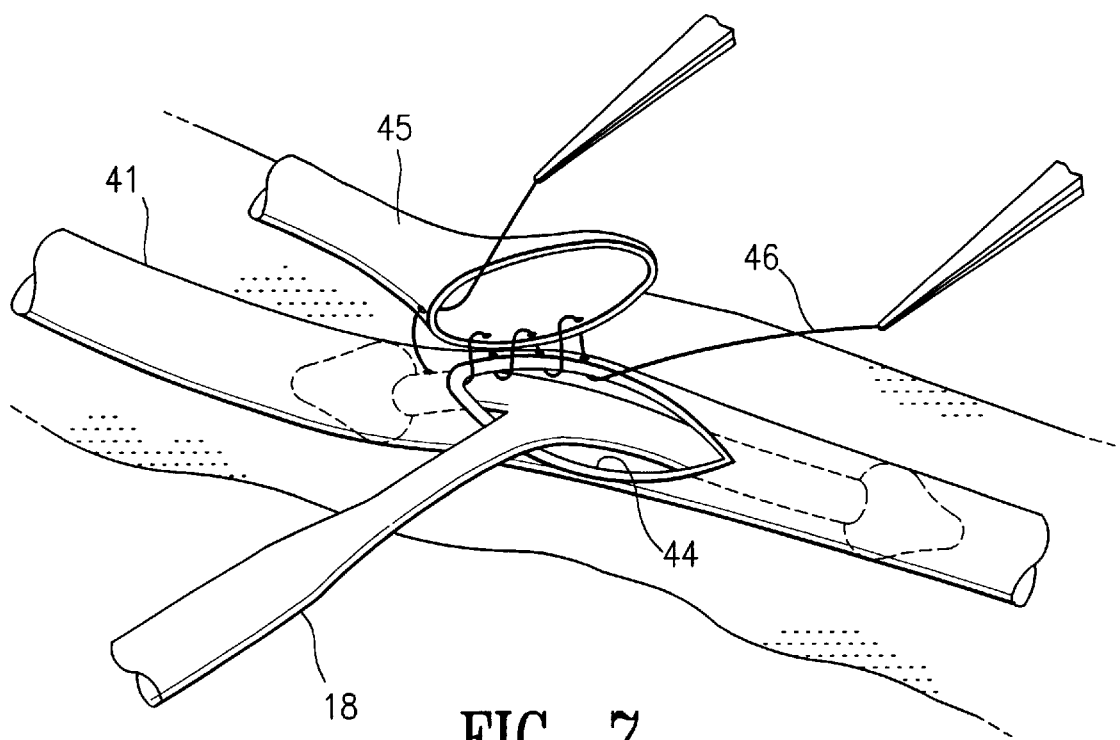
FIG. 7 illustrates the cannula shown in FIG. 6, during suturing of a bypass graft to the blood vessel.
Figure 8:
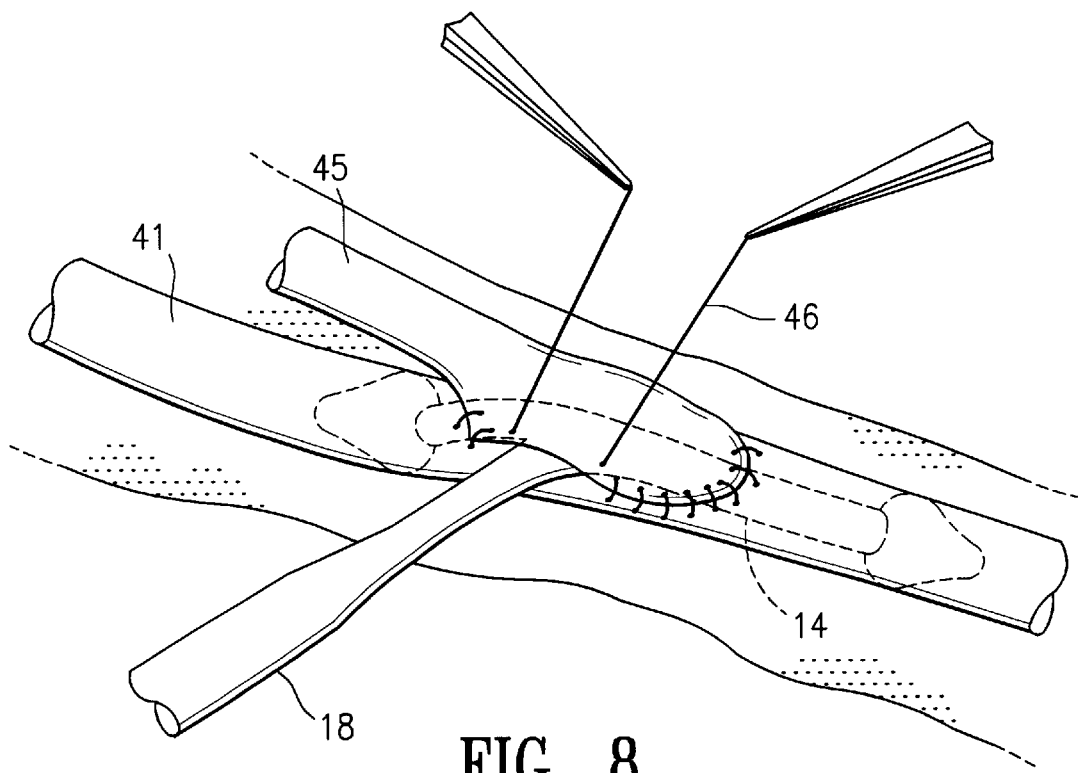
FIG. 8 illustrates the cannula shown in FIG. 7, nearing the completion of suturing of the bypass graft to the blood vessel.

The distal and proximal occluders 25/26 prevent or inhibit the flow of blood or perfusion fluid around the outer surface of the distal shaft section 14 in the artery 41, and in a presently preferred embodiment, occluders 25/26 have an outer diameter at a maximum dimension which is configured to contact the inner surface of the coronary artery. As a result, visualization of the anastomosis site is facilitated during attachment of a graft vessel to the coronary artery 41 at the incision 44. FIG. 7 illustrates a graft vessel 45 being sutured to the artery 41 with suture 46 around the incision 44, with the cannula 10 perfusing the myocardium distal to the incision 44 during the suturing. The expression "graft vessel" should be understood to include a variety of conventional implants including synthetic and natural prostheses, grafts and the like. Graft vessel 45 may comprises a variety of suitable materials, as are conventionally used in anastomosis procedures, including natural and synthetic materials, such as heterologous tissue, homologous tissue, polymeric materials, Dacron, and fluoropolymers, and polyurethanes, and the like. FIG. 8 illustrates the graft vessel 45 sutured to the artery 41 before the cannula 10 is removed and the final sutures are tied. The perfusion flow is stopped, and the cannula 10 is pulled proximally to remove the distal shaft section 14 from the coronary artery 41 and that exit is sutured to complete the suturing of the graft vessel 45 to the artery 41. The bypass surgery is completed by anastomosis of the other end of the graft vessel 45 to an artery section proximal to the lesion 42.

Figure 9:
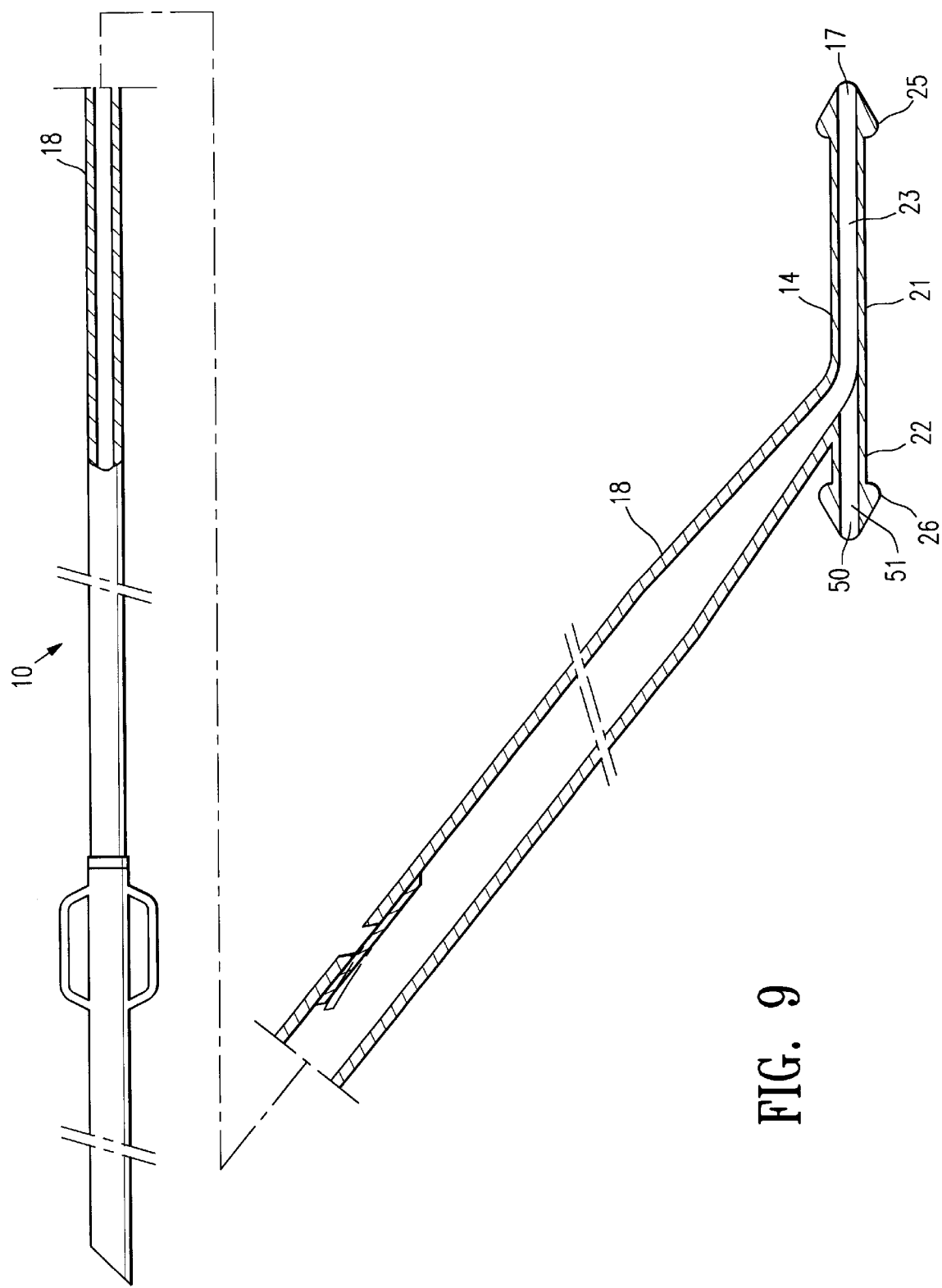
FIG. 9 is an elevational view, partially in section, of an alternative embodiment of a perfusion cannula which embodies features of the invention, having a lumen within a proximal portion of a distal shaft section of the cannula.

FIG. 9 illustrates an alternative embodiment of cannula 10 in which the proximal portion 22 has a port 50 in the proximal end of the distal shaft section 14 in fluid communication with a port in the distal end of the distal shaft section. In the embodiment illustrated in FIG. 9, a lumen 51 extends within the proximal portion 22 of the distal shaft section 14, and is in fluid communication with the lumen 23 in the distal portion 21 of the distal shaft section 14, so that the port 50 is in fluid communication with the port 17 in the distal end of the distal shaft section 14. The distal shaft section 14 thus provides a shunt within the coronary artery 41, to allow blood or perfusion fluid flow through the distal shaft section 14. However, the embodiment illustrated in FIG. 1 is a preferred embodiment, in situations where flow of perfusion fluid proximally out the port 50 in the proximal portion 22 would dislodge plaque producing embolization of particles in the patient's vasculature. As discussed above in relation to the embodiment of FIG. 1, proximal shaft section 18 is connected to distal shaft section 14 such that an acute angle is formed between the proximal shaft section 18 and proximal portion 22 of the distal shaft section 14 at the location of the connection therebetween.

In the embodiment illustrated in FIG. 1, the acute angle is about 40°. The acute angle between the proximal shaft section 18 and the proximal portion 22 of the distal shaft section 14 is about 20° to about 80°, and preferably about 25° to about 65°, and most preferably about 30° to about 50°. Due to the acute angle between the proximal and distal shaft sections, a distal portion of the proximal shaft section 18 of about 1 mm to about 4 mm is typically placed in contact with an outer surface of the artery 41 when the distal shaft section 14 is in place within the coronary artery 41.

The outer diameter of the enlarged portion of cannula at the occluders 25/26 is preferably about 0.2 mm less than or greater than the inner diameter of the native vessel, which provides for a good fit of the cannula distal shaft section in the native vessel.

The total working length of the cannula 10 and adapter 24 is about 20 cm to about 50 cm, preferably about 30 cm to about 40 cm. The length of the distal shaft section 14 is about 1.2 cm to about 3 cm, preferably about 1.5 cm to about 2 cm, and the length of the proximal shaft section 18 is about 20 cm to about 40 cm, preferably about 25 cm to about 35 cm. The distal shaft section 14 preferably has an outer diameter and an inner diameter which are sized to fit within a blood vessel to be treated and which are less than the outer diameter and inner diameter, respectively, of the proximal shaft section. The outer diameter of the distal shaft section (longitudinally displaced from and adjacent to occluders 25/26) is about 0.8 mm to about 2.5 mm, preferably about 0.9 mm to about 1.5 mm. The inner diameter of the distal shaft section (i.e., diameter of the lumen 23 therein) is about 0.7 mm to about 2 mm, preferably about 0.8 mm to about 1.5 mm, or about 20% to about 50% of the inner diameter of the proximal shaft section 18. The proximal shaft section has an outer diameter of about 4 mm to about 8 mm, and an inner diameter of about 2.5 mm to about 6.5 mm.

The cannula 10 may be provided in a variety of sizes with different occluder diameters sized to fit the inner diameters of different body lumens to be treated. The distal and proximal occluders 25/26 have an outer diameter at a maximum dimension thereof of about 1.25 mm to about 6 mm, preferably about 1.5 mm to about 4 mm. The proximal occluder is located about 8 mm to about 10 mm from the distal end of the distal shaft section 14, and the distal occluder is preferably at or about 1 to about 4 mm from the distal end of the distal shaft section.

The cannula shaft 11 may be formed of a variety of suitable materials conventionally used in formation of catheter shafts, including polyurethanes, polyolefines, polyamides, fluoropolymers, silicones, and polyvinyl chloride. In a presently preferred embodiment, the proximal and distal shaft sections are formed of silicon rubber. The proximal shaft section 18 typically has the same or less flexibility than the distal shaft section 14, and is preferably less flexible than the distal portion of the distal shaft section. Although the proximal shaft section may be flexible enough to have a proximal portion moveable relative to the distal shaft section, the proximal shaft section remains connected to the distal shaft section with an acute angle formed therebetween, as discussed above. Thus, the acute angle is the natural, biased position of the proximal shaft section relative to the distal shaft section.

While use of the catheter of the invention has been discussed in terms of a coronary bypass procedure, other applications exist, including perfusion of renal arteries such as during treatment of an abdominal aortic aneurysm, perfusion of visceral arteries such as during thoraco abdominal aneurysm resection, perfusion of peripheral and limb arteries such as after acute or traumatic occlusion to reduce the ischemic time until surgical reconstruction, and perfusion of selective organs or tissue such as for treatment of tumors.

While the invention has been described herein in terms of certain preferred embodiments, modifications and improvements may be made to the invention without departing from the scope thereof. While discussed in terms of delivering an oxygenated fluid such at blood to a patient's blood vessel, the cannula of the invention can be used to deliver other therapeutic or diagnostic fluids when the proximal end is connected to a source of such fluids. Moreover, while individual features may be discussed or shown in relation to a specific embodiment, the individual features may be used in the other embodiments of the invention.

What is claimed is:

1. A method of performing a medical procedure, comprising the steps of:
    a) providing a perfusion cannula comprising
       an elongated shaft having a distal shaft section implanted within a body lumen having a closed proximal end, a distal end and a port in the distal end of the distal shaft section; and a proximal shaft section having a proximal and distal end, the distal end implanted within a body lumen and which is connected to the distal shaft section at a location between the proximal and distal ends of the distal shaft section, such that an acute angle is formed at the location at which the proximal shaft section is connected to the distal shaft section, the acute angle being between the proximal shaft section and a proximal portion of the distal shaft section; and
    a lumen in the elongated shaft which extends within the proximal shaft section and within at least a portion of the distal shaft section to and in fluid communication with the port in the distal end of the distal shaft section;
    b) inserting the distal shaft section through an incision in a patient's blood vessel and into the blood vessel at a location distal to an occlusion in the blood vessel, so that a section of the blood vessel at a proximal end of the incision therein is located between and in contact with the proximal shaft section and the proximal portion of the distal shaft section; and
    c) connecting the proximal end of the perfusion cannula to a source of perfusion fluid, so that perfusion fluid flows from the proximal shaft section to the distal shaft section and out the port in the distal end of the distal shaft section.

2. The method of claim 1 wherein the distal shaft section includes a proximal occluder on the proximal portion and a distal occluder on the distal portion, and including after c), attaching an end of a graft vessel to the patient's blood vessel at the opening therein.

3. The method of claim 1 including a guidewire slidably disposed in the shaft lumen, and wherein inserting the distal shaft section through the opening comprises advancing the distal shaft section with the guidewire therein into the blood vessel.

4. The method of claim 1 wherein the shaft includes an intermediate guidewire port on the proximal shaft section between the proximal and distal ends of the shaft, and including a guidewire having a proximal end extending out the intermediate guidewire port and a distal end extending out the port in the distal end of the distal shaft section, and wherein inserting the distal shaft section through the opening comprises advancing the distal shaft section with the guidewire therein into the blood vessel.

5. The method of claim 1 wherein the closed proximal end of the distal shaft section is solid.

6. A perfusion cannula, comprising:
    a) an elongated shaft having
       i) a distal shaft section having a closed proximal end, a distal end, a first port in the distal end; and
       ii) a proximal shaft section which is connected to the distal shaft section at a location between the proximal and distal ends of the distal shaft section, such that an acute angle is formed at the location at which the proximal shaft section is connected to the distal shaft section, the acute angle being between the proximal shaft section and a proximal portion of the distal shaft section; and
    b) a lumen in the elongated shaft which extends within the proximal shaft section and within at least a portion of the distal shaft section to and in fluid communication with the first port in the distal end of the distal shaft section.

7. A perfusion cannula, comprising:
a) an elongated shaft having
   i) a distal shaft section having a closed proximal end, a distal end, a first port in the distal end of the distal shaft section; and
   ii) a proximal shaft section which is connected to the distal shaft section at a location between the proximal and distal ends of the distal shaft section, such that an acute angle is formed at the location at which the proximal shaft section is connected to the distal shaft section, the acute angle being between the proximal shaft section and a proximal portion of the distal shaft section; and
b) a lumen in the elongated shaft which extends within the proximal shaft section and at least a portion of the distal shaft section and which is unobstructed and in fluid communication with the first port in the distal end of the distal shaft section.

8. A perfusion device, comprising:
a. a first tubular shaft which is configured to be implanted within a patient's body lumen, which has a distal shaft portion having a distal end, a first port in the distal end, an opening in a side wall of the first tubular shaft at an intermediate location between proximal and distal ends thereof, an inner lumen extending to and in fluid communication with the first port in the distal end and the opening in the side wall and which has a proximal shaft portion having an closed proximal end and no lumen in communication with the inner lumen in the distal shaft section; and
b. a second tubular shaft which has a proximal end, which has a distal end secured to the first tubular shaft at the intermediate location of the first tubular member, which has an opening in the distal end, which has an inner lumen extending therein to and in fluid communication with the opening in the distal end and with the inner lumen of the first tubular member through the opening in the distal end and the opening in the side wall of the first tubular shaft.

9. The cannula of claim 8, wherein the proximal shaft portion is a solid member.

10. The cannula of claim 8 wherein the distal shaft section has enlarged occluding proximal and distal ends.

11. The cannula of claim 10 wherein the enlarged distal end of the distal shaft section has a larger outer diameter than a portion of the distal shaft section proximal thereto.

12. The cannula of claim 11 wherein the enlarged distal end of the first tubular shaft tapers proximally to the smaller outer diameter portion.

13. The cannula of claim 10 wherein the enlarged proximal end of the distal shaft section has a larger outer diameter than a portion of the distal shaft section distal thereto.

14. The cannula of claim 13 wherein the enlarged proximal end tapers distally to the smaller outer diameter portion.

15. The cannula of claim 8 including an adapter at the proximal end of the second shaft section configured for connection to a source of perfusion fluid.

16. The cannula of claim 15 wherein the adapter comprises a needle configured for insertion into a patient's blood vessel.

17. The cannula of claim 8 wherein the second tubular shaft has an intermediate guidewire port between the proximal and distal ends thereof.

18. The cannula of claim 17 wherein the second tubular shaft includes a blocking member at the intermediate guidewire port configured to block flow of fluid from the lumen of the second tubular shaft out the intermediate guidewire port.

19. The cannula of claim 8 wherein the second tubular shaft inclines toward the proximal shaft portion of the first tubular shaft at an acute angle of about 20° to about 80°.

20. The cannula of claim 8 wherein the first tubular shaft has a length of about 12 mm to about 30 mm.

21. The cannula of claim 8 wherein the second tubular shaft has a length of about 20 mm to about 50 mm.

22. The cannula of claim 8 wherein the second tubular shaft has a larger outer diameter and a larger inner diameter than the first tubular shaft.

23. The cannula of claim 8 wherein a distal portion of the first tubular shaft has an inner diameter about 20% to about 50% of an inner diameter of the second tubular shaft.

24. A perfusion device, comprising:
a. a first tubular shaft which is configured to be implanted within a patient's body lumen, which has a distal shaft portion having a distal end a first port in the distal end, an opening in a side wall of the first tubular shaft at an intermediate location between proximal and distal ends thereof, an inner lumen extending to and in fluid communication with the first port in the distal end and the opening in the side wall and which has a proximal shaft portion having an solid proximal end and no lumen in communication with the inner lumen in the distal shaft section; and
b. a second tubular shaft which has a proximal end, which has a distal end secured to the first tubular shaft at the intermediate location of the first tubular member, which has an opening in the distal end, which has an inner lumen extending therein to and in fluid communication with the opening in the distal end and with the inner lumen of the first tubular member through the opening in the distal end and the opening in the side wall of the first tubular shaft.

25. The cannula of claim 24 wherein the proximal shaft section is connected to the distal shaft section at a location on the distal shaft section between the proximal and distal ends of the distal shaft section.

26. The cannula of claim 25 wherein an acute angle is formed at the location at which the proximal shaft section is connected to the distal shaft section, the acute angle being between the proximal shaft section and the proximal portion of the distal shaft section.

* * * * *